US009125556B2

(12) United States Patent
Zehavi et al.

(10) Patent No.: US 9,125,556 B2
(45) Date of Patent: Sep. 8, 2015

(54) ROBOTIC GUIDED ENDOSCOPE

(71) Applicant: MAZOR ROBOTICS LTD., Caesaria (IL)

(72) Inventors: Eli Zehavi, Haifa (IL); Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 71 days.

(21) Appl. No.: 13/893,366

(22) Filed: May 14, 2013

(65) Prior Publication Data

US 2013/0303883 A1 Nov. 14, 2013

Related U.S. Application Data

(60) Provisional application No. 61/688,418, filed on May 14, 2012.

(51) Int. Cl.
| | | |
|---|---|---|
| A61B 1/00 | (2006.01) | |
| A61B 8/08 | (2006.01) | |
| A61B 6/03 | (2006.01) | |
| G01R 33/28 | (2006.01) | |
| A61B 6/00 | (2006.01) | |
| A61B 19/00 | (2006.01) | |
| A61B 6/12 | (2006.01) | |
| A61B 17/00 | (2006.01) | |

(52) U.S. Cl.
CPC ............... *A61B 1/00154* (2013.01); *A61B 6/12* (2013.01); *A61B 6/485* (2013.01); *A61B 6/487* (2013.01); *A61B 6/5247* (2013.01); *A61B 19/2203* (2013.01); *G01R 33/285* (2013.01); *A61B 6/032* (2013.01); *A61B 8/0841* (2013.01); *A61B 19/201* (2013.01); *A61B 2017/00261* (2013.01); *A61B 2019/5295* (2013.01); *A61B 2019/5466* (2013.01); *A61B 2019/5483* (2013.01)

(58) Field of Classification Search
CPC ............. A61B 19/201; A61B 19/2203; A61B 1/00154; A61B 2017/00261; A61B 2019/5295; A61B 2019/5466; A61B 2019/5483; A61B 6/032; A61B 6/485; A61B 6/5247; A61B 8/0841; G01R 33/285
USPC .................. 600/417, 424; 606/86 R, 130, 279
See application file for complete search history.

(56) References Cited

U.S. PATENT DOCUMENTS

| | | | | |
|---|---|---|---|---|
| 7,887,567 B2 * | 2/2011 | Shoham et al. | ............... | 606/279 |
| 2008/0243142 A1 * | 10/2008 | Gildenberg | ................... | 606/130 |

* cited by examiner

*Primary Examiner* — Michael Rozanski
(74) *Attorney, Agent, or Firm* — Daniel J. Swirsky; AlphaPatent Associates Ltd.

(57) ABSTRACT

Systems and methods for performing robotic endoscopic surgical procedures, according to a surgical plan prepared on a preoperative set of three dimensional images. The system comprises a surgical robot whose coordinate system is related to that of fluoroscope images generated intraoperatively, by using a three dimensional target having radio-opaque markers, attached in a predetermined manner to the robot or to another element to which the robot is attached, such as the spinal bridge or an attachment clamp. The robot is mounted directly or indirectly on a bone of the patient, thereby nullifying movement of the bone, or a bone tracking system may be utilized. The coordinate system of the intraoperative fluoroscope images may be related to the preoperative images, by comparing anatomical features between both image sets. This system and method enables the endoscope to be directed by the robot along the exact planned path, as determined by the surgeon.

11 Claims, 4 Drawing Sheets

ROBOTIC GUIDED ENDOSCOPE

CROSS-REFERENCE TO RELATED APPLICATIONS

This application claims the benefit of priority from U.S. Provisional Patent Application No. 61/688,418, titled "Robotic Guided Endoscope," and filed on May 14, 2012, the contents of which are incorporated herein by reference in their entirety.

FIELD OF THE INVENTION

The present invention relates to the field of robotically guided endoscopic procedures, especially for use in orthopedic procedures performed on the spine.

BACKGROUND OF THE INVENTION

Endoscopes are a prime element used in order to achieve Minimally Invasive Surgery (MIS). However, it has been difficult to achieve dexterity and precision of instrument control within the confines of a limited operating space, further compounded by the need to operate from a 2D video image. The application of robotic technology has the potential to contribute significantly to the advancement of endoscopic spine surgery.

As described in the section on "Robotics: An Approach to Minimally Invasive Spine Surgery", http://bme240.eng.uci.edu/students/10s/sgupta1/RobotSpineSurgery.html in the section entitled "Application of Robotics to Endoscopic Spine Surgery" in the course on Introduction to Clinical Medicine at the University of California at Irvine, there is described the use of a surgical robot with haptic control for this purpose, having several distinct and compelling advantages, which suggests that this particular technology is capable of significantly enhancing current operative technique. Unlike conventional instrumentation which requires manipulation in reverse, the proportional movement of the robotic device allows the instruments to follow the movement of the surgeon's hands directly. The intuitive control of the instruments is particularly advantageous for the novice endoscopist. In addition to mimicking the surgeon's movements in an intuitive manner, the robotic instruments offer six degrees of freedom plus grip, two more than conventional instruments. This technology permits a large range of motion and rotation that follows the natural range of articulation of the human wrist and may be particularly helpful when working space is limited. The electronic control system is capable of filtering out hand tremors as well as motion scaling, whereby gross hand movements at the surgeon's console may be translated to much finer movement of the instrument tips at the operative site. The 3D vision system adds a measure of safety and surgical control beyond what is available with the traditional endoscope. The 3D display improves depth perception, and the ability to magnify images by a factor of 10 allows extremely sensitive and accurate surgical manipulation. The alignment of the visual axis with the surgeon's hands in the console further enhances hand-eye coordination to a degree uncommon in traditional endoscopic surgery.

All of these features are related to the advantages of robotic endoscopy in providing haptic and visual support to the surgeon once the procedure is in progress. However, another area so far untackled is the need to provide accurate access for the endoscope to the operation site, in order to reduce the trauma of the procedure. If an incision for an endoscopic procedure is made in the patient's soft tissue in the incorrect position or at an incorrect angle, it is difficult to make an intraoperative correction to reach the required operating site without either significantly enlarging the extent of the incision, or withdrawing and making a second incision to gain more accurate access to the operating site. This problem is particularly acute for operations performed on the spine, such as percutaneous discectomy. In this procedure, an annular tear, bulging disc, or herniated disc which is compressing a nerve may be accessed using an endoscopic technique, and a laser or knife used to correct the tear or remove the bulge. After the damaged portion of the disc has been removed, the laser vaporizes the surrounding area, and can shrink and remodel the remaining disc. Because of the closeness of the operating site and its access paths to major and critical nerve structures, high positional accuracy of the endoscope insertion path is required.

There therefore exists a need for a robotic endoscopic apparatus and procedure which will provide adequate solutions to these problems, and especially to reduce the level of surgeon skill required to maintain minimally invasive conditions.

The disclosures of each of the publications mentioned in this section and in other sections of the specification, are hereby incorporated by reference, each in its entirety.

SUMMARY OF THE INVENTION

The present disclosure describes new exemplary systems and methods for performing endoscopic surgical procedures with a level of accuracy which reduces the trauma which may be involved in the procedure. The system typically comprises a surgical robot whose position is fixed relative to the patient's bone, according to one implementation, by mounting the robot either directly or partially on a bone of the patient.

The relation of the robot pose co-ordinate system relative to the co-ordinate system of fluoroscope images taken during the procedure (intraoperative), can be determined by using a three dimensional target having radio-opaque markers, whose pose can therefore be determined in the fluoroscope images, the target being attached in a predetermined manner either to the robot itself, or to another element to which the robot is attached, such as a spinal bridge or an attachment clamp.

The method of mounting a miniature robot directly on the bone provides a convenient and compact implementation of this procedure, and is described in U.S. Pat. No. 6,837,892 for "Miniature Bone-attached Surgical Robot". Other methods which involve attaching the robot to a bridge structure which is supported partly or wholly on bones of the patient are described in U.S. Pat. No. 7,887,567 for "Apparatus for Spinal Fixation of Vertebrae", and a further support method is shown in co-pending PCT International Patent Application No. PCT/IL2012/000387 for "Active Bed Mount for Surgical Robot". All of these methods completely or largely eliminate the effect of motion of the patient's bone during the operation.

Alternatively, an independently mounted robot, such as a floor mounted robot, can be used, whose pose relative to the bone of the patient is known, such as by means of a navigational system which can relate the position of the bone to that of the robot by means of fiducial reference markers on the bone and on the robot end effector, which can be tracked by the navigational system, or by use of a mechanical bone-following arm, which may be attached to a point on the bone, and which tracks mechanical motion of the bone by use of angular and linear sensors in the arm, as is known in the art.

The preoperative images of the surgical site, on which the surgeon has planned the procedure to be performed by the endoscope, can be related with the images actually generated intraoperatively, and also the co-ordinate system of the preoperative images of the surgical site can be related in a known manner to the co-ordinate system of the intra-operative fluoroscope images, and hence also the co-ordinate system of the robot, by comparing anatomical features shown in the two sets of images. However, this is only one method of performing this registration procedure, and any other registration procedure known in the art may also be used.

Use of such a surgical robot enables the endoscope to be directed at the exact point desired, as determined by the surgeon. The surgeon, using preoperative images of the operation site, such as CT images, plans the exact entry position and the angular orientation of the endoscope port, such that it reaches the operation site without impacting with or even passing too close to any sensitive anatomical features in its entry path. During the operation itself, the robot can therefore be controlled to direct the endoscope cannula to its intended entry position and along in its intended path, using only two or sometimes somewhat more intra-operative fluoroscopic images to achieve correct registration of the robot to the preoperative CT images. By this means, the entire endoscopic procedure can be performed with minimal trauma to the patient's soft tissues, since the initial entry should accurately and safely position the endoscope so that the surgical tool is correctly positioned for the intended operation.

One exemplary implementation involves a method of guiding an endoscope to an orthopedic surgical site, comprising:

(i) generating preoperative images of the orthopedic surgical site, and planning the entry trajectory of the endoscope according to the preoperative images, (ii) mounting a surgical robot such that it has a fixed location relative to the orthopedic surgical site, (iii) attaching a three dimensional target to the robot or to an attaching structure providing the robot with its fixed location relative to the orthopedic surgical site, (iv) generating at least two intraoperative fluoroscope images of the orthopedic surgical site, the images including at least a major part of the three dimensional target, such that the orientation of the target in the co-ordinate system of the fluoroscope images can be calculated from the three dimensional marker images, (v) from the position and orientation of the target, determining the position and orientation of the robot or of its attaching structure in the co-ordinate system of the fluoroscope images, (vi) relating the fluoroscope image co-ordinate system to the preoperative images by comparison of anatomic features on the images, such that the planned entry trajectory is also defined in the co-ordinate system of the robot, (vii) providing instructions to the robot to adopt a pose such that a guidance tube held in its operating arm is aligned along the planned trajectory, and (viii) using that robotic pose to insert the endoscope along the planned trajectory.

In that method, the preoperative images may be any one of CT or MRI or Ultrasound images. Furthermore, the robot may be mounted directly on a bone of the orthopedic surgical site, and the three dimensional target attached to the robot, or alternatively, an attaching structure may attached to the orthopedic surgical site, and the intraoperative fluoroscope images taken with the target mounted on the attaching structure, and the robot may then be attached to the structure in place of the target after generation of the intraoperative fluoroscope images. In either of these cases, the attaching structure may a bone attachment clamp for clamping the robot directly to a bone in the orthopedic surgical site or a spinal bridge attached to a patient's spine at at least one vertebra, and wherein the robot is mounted on the spinal bridge.

In yet other implementations of the above-described methods, the three dimensional target may comprise a plurality of radio-opaque markers, arranged in a predetermined three dimensional pattern.

In any of these methods, the endoscope may be inserted along the planned trajectory by first preparing an incision along the planned trajectory using a scalpel inserted along a guide cannula held in the appropriate pose by the robot, and thereafter enlarging the incision to take the endoscope cannula. Furthermore, the robot and any of its support structures may be removed before insertion of the endoscope, once the planned trajectory has been defined by robotic insertion of a guiding element, which could conveniently be a K-wire.

BRIEF DESCRIPTION OF THE DRAWINGS

The invention will be understood and appreciated more fully from the following detailed description, taken in conjunction with the drawings in which.

DETAILED DESCRIPTION OF THE INVENTION

Figure 1:
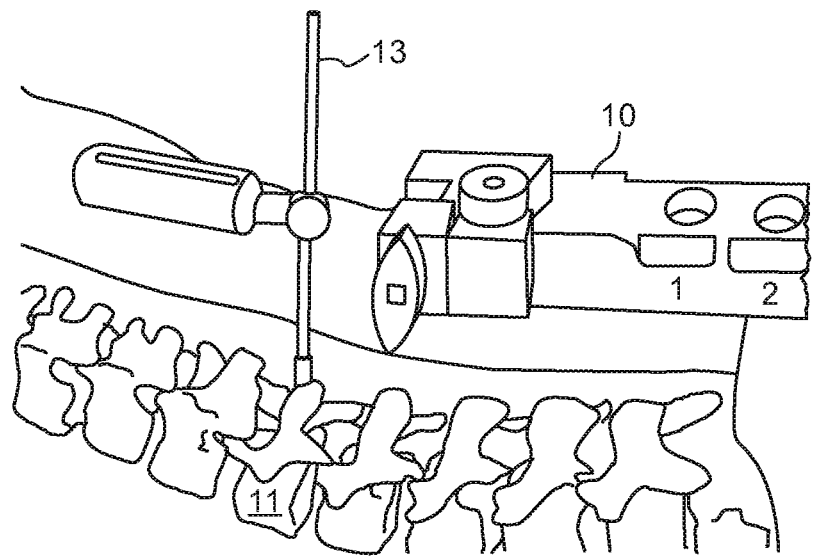
FIG. 1 shows schematically how the bone supported end of a robotic bridge is fixed to one of the vertebrae of the subject.

The following description is based on an exemplary spinal operation implementation in which the robot is mounted on a bridge element having a number of predetermined attachment positions for the robot. The bridge may be supported at one end on a vertebra of the patient and at the other end on a support post rigidly mounted to the bed (to be shown in FIG. 5). It is to be understood though that this is merely one exemplary procedure and method of supporting the robot, and the invention is not intended to be limited to spinal procedures or to this particular method. Reference is now made to FIG. 1, which illustrates schematically (on a phantom of the spine so that the exact subcutaneous procedure can be followed) how the bone supported end of the robotic bridge 10 can be fixed to one of the vertebrae 11 of the subject. A hole is drilled, preferably into the spinous process in the region of the operating site, and a supporting pin 13 is screwed in, by means of which the end of the bridge is attached to the vertebra.

Figure 2:
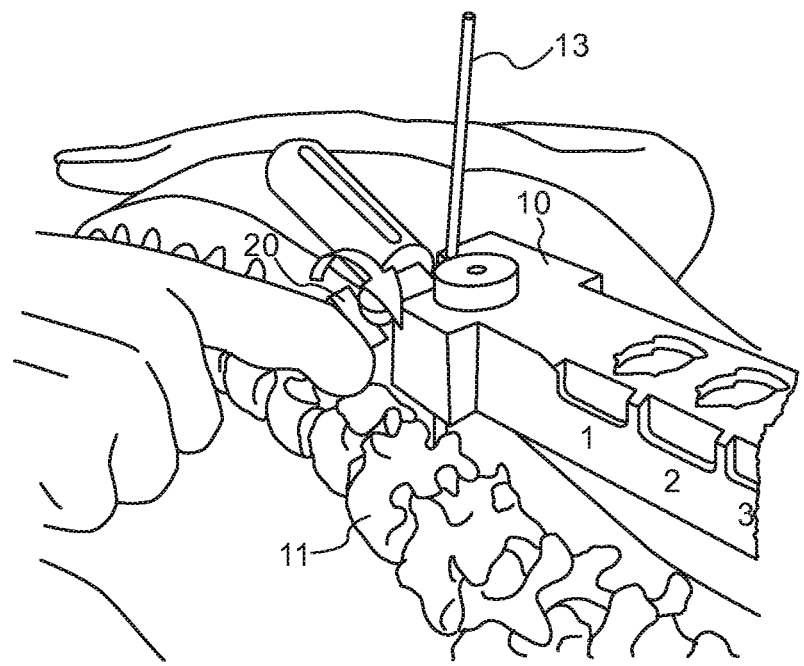
FIG. 2 shows schematically the end of the robotic bridge attached to a supporting pin in the subject's vertebra.

FIG. 2 shows schematically, how the end of the bridge 10 may be offered up to the supporting pin 13 and the attachment thumb screw 20 tightened up to provide a rigid relationship between the end of the bridge and the vertebrae.

Figure 3:
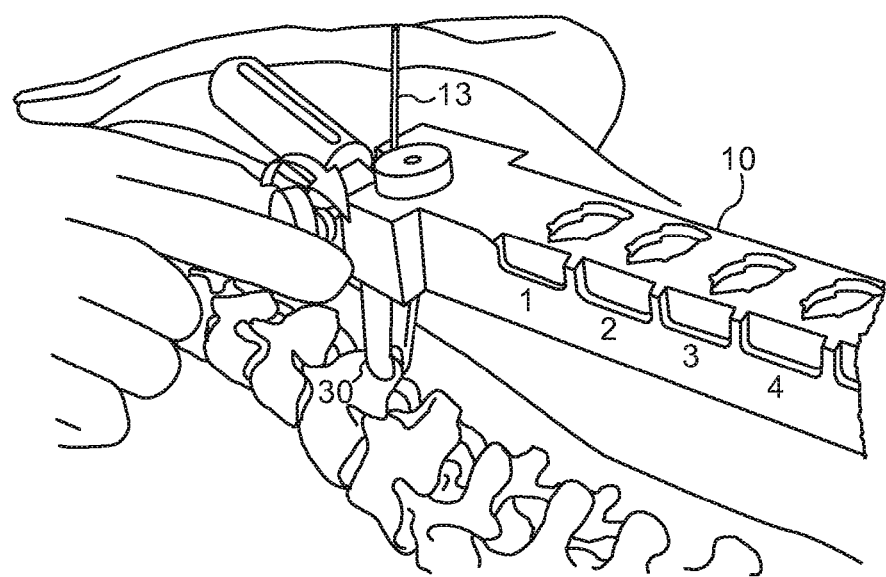
FIG. 3 shows an alternative method of clamping the end of the bridge to the vertebra, using a bone clamp.

FIG. 3 shows an alternative method of clamping the end of the bridge to the spinous process, using a bone clamp 30 attached to the spinous process. Such a clamp attachment method would generally require a larger incision than a pin attachment.

Figure 4:
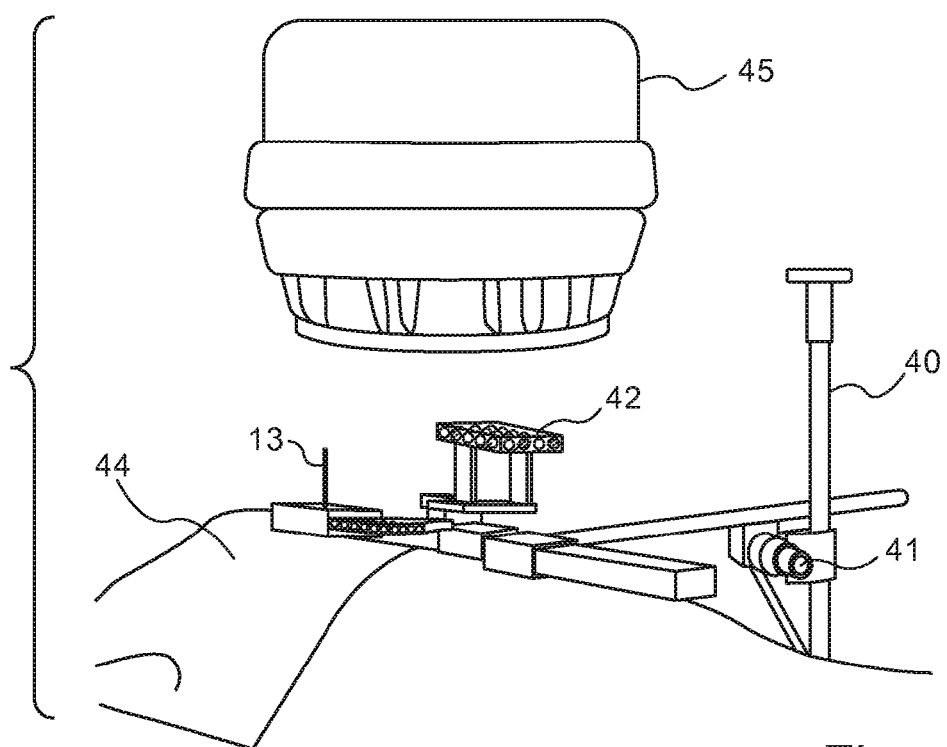
FIG. 4 shows schematically the bridge attached in position on the patient's back with one end attached to the support pin, and the other end attached to a bed-mounted support post, and a three-dimensional target attached for correlating the co-ordinate systems of the C-arm and the robot.

In FIG. 4, there is now shown the bridge attached in position on the patient's back 44 with one end attached to the support pin 13 which is shown in this example, affixed into one of the patient's vertebra, and the other end attached to a bed-mounted support post 40, by means of a rotary joint 41. The 3-dimensional target 42 is shown in this exemplary implementation having radio-opaque marker balls with known positions disposed in two different planes, and is shown attached to the bridge in a predetermined position. When the C-arm camera 45 takes images of the Region of Interest, which should include at least a major part of the target and the vertebrae, for instance, that are to be operated on, the known positions of the radio-opaque balls in the target can be used by the controller program to define the three-dimensional position of the bridge in the intra-operative fluoroscope images. Consequently, since the robot will be attached to the bridge in a predetermined location, its three dimensional position relative to the co-ordinate system of the intra-operative fluoroscope images will also be known. In general, fluoroscope images of the 3-dimensional target taken at 2 different angles are sufficient to fully define the robotic frame of reference relative to the C-arm frame of reference. Since the image comparison routine enables the fluoroscope images to be registered to the preoperative CT images, this means that the robot pose can be defined relative to the pre-operative images. Consequently, the pre-planned entry point and entry angles of the endoscope cannula can be defined in real time by the robot pose, and the surgical tools required will be accurately aligned for achieving this insertion.

Figure 5:
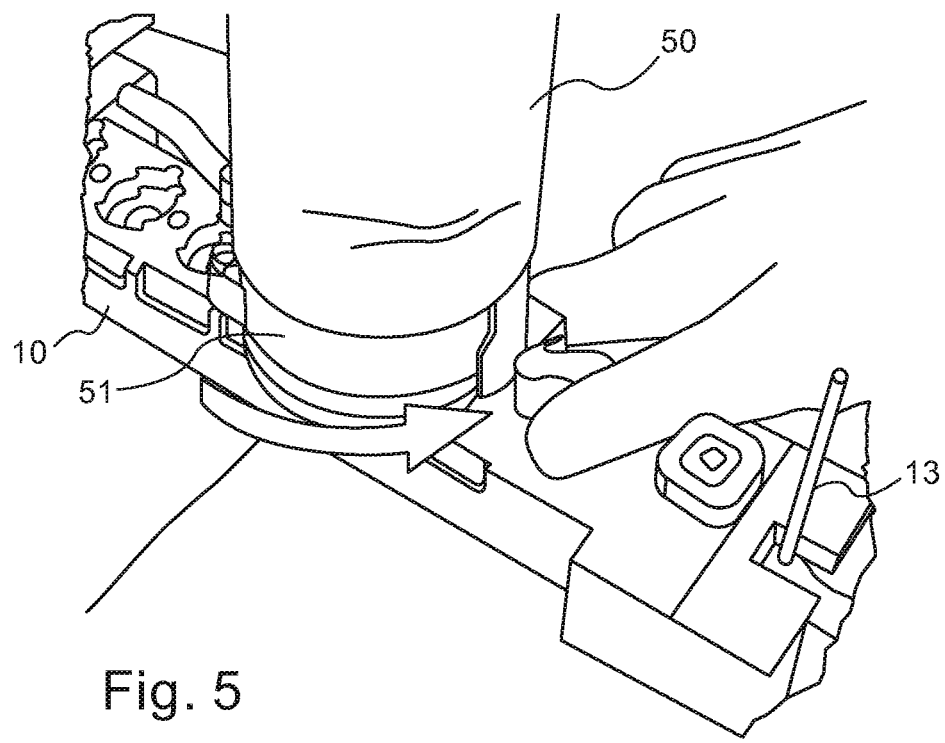
FIG. 5 shows schematically how a miniature surgical robot is attached to the bridge element by its base in a predefined position.

Reference is now made to FIG. 5, which shows how a miniature surgical robot 50 is attached to the bridge element 10 by its base 51 in a predefined position, so that the robot's geometric base co-ordinates are defined relative to the bridge 10, which the target registration procedure has defined relative to the preoperative images and hence the surgical plan. The surgeon is then able to use the system software program in order for the robot to align itself in the correct position and at the correct angle to generate the correct trajectory for the endoscope insertion procedure.

Figure 6:
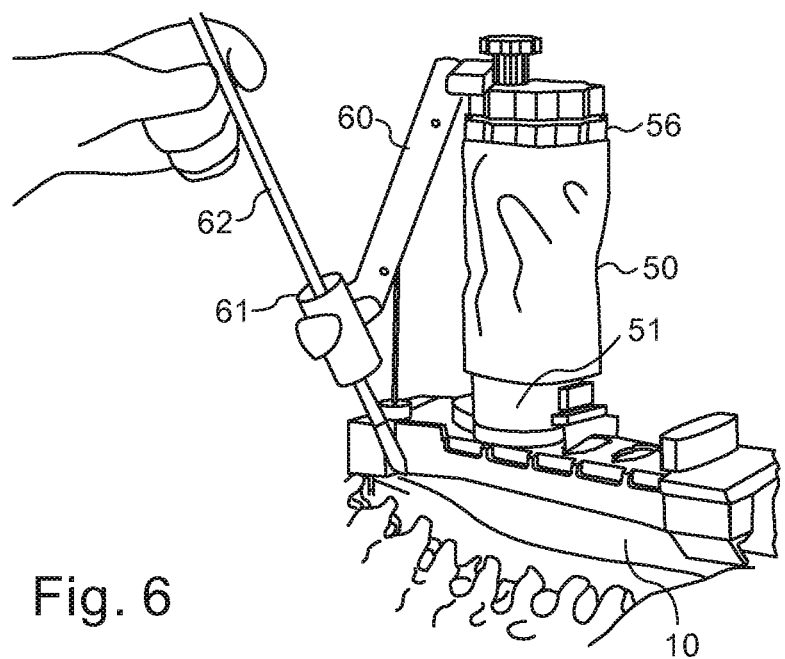
FIG. 6 shows the insertion of the incision scalpel down the robotically directed guide tube.

The initial step of the endoscopic surgical procedure is shown in FIG. 6. The actuation arm 60 of the robot is shown attached to the driven platform 56 of the robot, which responds in accordance with the input signals from the robot controller. Attached thereto is a guide tube 61, through which the various surgical tools are directed to perform their function in the desired direction and location. First of all, a scalpel 62 can be inserted to perform the initial incision through the patient's dorsal fascia. The guide tube for the scalpel may have a bore adapted to take the size of the scalpel blade.

Once the appropriate incision has been made, the scalpel guide tube (if such is used) may be replaced by a cannula guide tube, carefully avoiding any disturbance to the robotically locked pose of the robot arm. A Blunt can then be inserted for enlarging the slit incision and for clearing a path through the muscles for the guide cannula. Once the Blunt has been inserted so that it hits the bone, the guide cannula can be inserted to its predetermined depth, and the Blunt can then be removed. The endoscope cannula, through which the endoscope itself will be passed, can then be inserted into the guide cannula. A reduction tube can then be inserted to define the bore more accurately. At this point, the position and depth of the inserted tubes can be verified by fluoroscope images, both AP and Oblique. A K-wire can then be inserted into the reduction tube, and gently tapped into the bone, after which the reduction tube can be removed leaving the K-wire in its correct position and orientation. At this point, the robot with its bridge assembly can be removed, since the desired position and orientation for the endoscope entry has been correctly defined by the K-wire. Dilators can then be mounted sequentially on top of the K-wire, until the endoscope can be inserted into the desired location.

Figure 7:
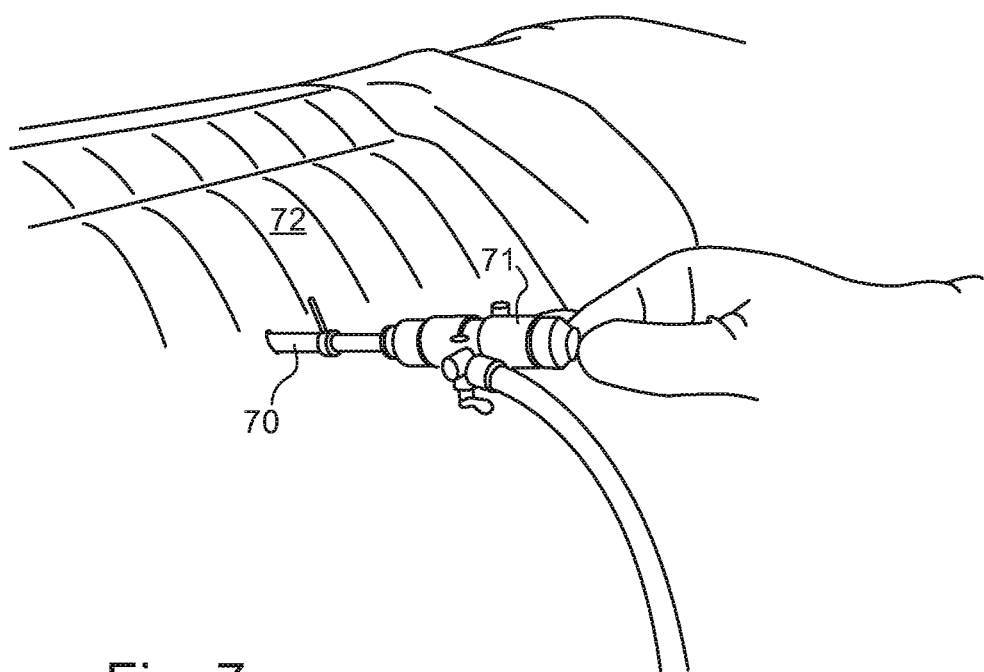
FIG. 7 is a schematic drawing showing the endoscope guide tube and endoscope correctly positioned in the back of the patient.

Reference is now made to FIG. 7, which is a schematic drawing showing the endoscope guide tube 70 and endoscope 71 correctly positioned in the back 72 of the patient. It is noted that the angle and position of entry path are substantially divergent from the centerline of the patient's back, showing how the above described robotic method is able to maintain positional accuracy in three dimensions over long insertion paths. Subcutaneous insertion paths of over 250 mm. can readily be achieved with high target point accuracy.

It is appreciated by persons skilled in the art that the present invention is not limited by what has been particularly shown and described hereinabove. Rather the scope of the present invention includes both combinations and sub combinations of various features described hereinabove as well as variations and modifications thereto which would occur to a person of skill in the art upon reading the above description and which are not in the prior art.

We claim:

1. A method of guiding an endoscope to an orthopedic surgical site, comprising:

generating preoperative images of the orthopedic surgical site, and determining a planned trajectory of the endoscope according to the preoperative images;

mounting a surgical robot such that it has a fixed location relative to the orthopedic surgical site;

attaching a three dimensional target to the robot or to an attaching structure providing the robot with its fixed location relative to the orthopedic surgical site;

generating at least two intraoperative fluoroscope images of the orthopedic surgical site, said at least two intraoperative fluoroscope images including at least a major part of said three dimensional target, such that the orientation of the target in the co-ordinate system of said fluoroscope images can be calculated from the three dimensional target;

from the position and orientation of the target, determining the position and orientation of the robot or of its attaching structure in the co-ordinate system of said fluoroscope images;

relating the fluoroscope image co-ordinate system to the preoperative images by comparison of anatomic features on said at least two intraoperative fluoroscope images, such that the planned trajectory is also defined in the co-ordinate system of the robot;

providing instructions to the robot to adopt a pose such that a guidance tube held in its operating arm is aligned along the planned trajectory;

preparing an incision along the planned trajectory using a scalpel inserted along said guidance tube and enlarging the incision to a size suitable to accommodate said endoscope;

using said robot pose to insert a guiding element along said planned trajectory, and removing said robot and any of its support structures; and using said guiding element to insert the endoscope along the planned trajectory.

2. A method according to claim 1 wherein said preoperative images are any one of CT or MRI or Ultrasound images.

3. A method according to claim 1, wherein the robot is mounted directly on a bone of the orthopedic surgical site, using said attaching structure, and the three dimensional target is attached to the robot.

4. A method according to claim 3, wherein the attaching structure is a bone attachment clamp for clamping the robot directly to a bone in the orthopedic surgical site.

5. A method according to claim 3, wherein the attaching structure is a spinal bridge attached to a patient's spine at at least one vertebra, and wherein the robot is mounted on the spinal bridge.

6. A method according to claim 1, wherein said attaching structure is attached to the orthopedic surgical site, and the intraoperative fluoroscope images are taken with the target mounted on the attaching structure, and the robot is attached to the structure in place of the target after generation of the intraoperative fluoroscope images.

7. A method according to claim 6, wherein the attaching structure is a bone attachment clamp for clamping the robot directly to a bone in the orthopedic surgical site.

8. A method according to claim 6, wherein the attaching structure is a spinal bridge attached to a patient's spine at at least one vertebra, and wherein the robot is mounted on the spinal bridge.

9. A method according to claim 1, wherein the three dimensional target comprises a plurality of radio-opaque markers, arranged in a predetermined three dimensional pattern.

10. A method according to claim 1 wherein said guiding element is a K-wire.

11. A method according to claim 1 wherein said guiding element is an endoscope guide tube.

\* \* \* \* \*